United States Patent
Boese et al.

(10) Patent No.: US 7,460,642 B2
(45) Date of Patent: Dec. 2, 2008

(54) METHOD FOR GENERATING AN X-RAY IMAGE SEQUENCE

(75) Inventors: Jan Boese, Eckental (DE); Norbert Rahn, Forchheim (DE); Bernhard Sandkamp, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 155 days.

(21) Appl. No.: 11/478,464

(22) Filed: Jun. 29, 2006

(65) Prior Publication Data

US 2007/0003017 A1    Jan. 4, 2007

(30) Foreign Application Priority Data

Jun. 29, 2005    (DE) .................. 10 2005 030 364

(51) Int. Cl.
   *H05G 1/42*    (2006.01)
(52) U.S. Cl. ..................... 378/97; 378/108
(58) Field of Classification Search .......... 378/97, 378/95, 98.7, 108, 62, 110, 112, 109, 207
   See application file for complete search history.

(56) References Cited

U.S. PATENT DOCUMENTS 5,919,135 A * 7/1999 Lemelson ............... 600/407
6,563,909 B2    5/2003 Schmitz
7,127,030 B2 * 10/2006 Tamegai ..................... 378/97
7,194,065 B1 * 3/2007 Boutenko et al. .......... 378/108
2004/0081341 A1    4/2004 Cherek et al.
2005/0013410 A1    1/2005 Hornegger

FOREIGN PATENT DOCUMENTS

| DE | 199 62 281 A1 | 6/2001 |
| DE | 102 32 676 A1 | 1/2004 |
| DE | 103 24 905 A1 | 12/2004 |
| DE | 103 27 293 A1 | 1/2005 |
| EP | 1 430 835 A1 | 6/2004 |
| EP | 1 444 952 A1 | 8/2004 |
| WO | WO 03/059166 A2 | 7/2003 |

\* cited by examiner

Primary Examiner—Hoon Song

(57) ABSTRACT

With a method for generating an x-ray image sequence for supporting an intervention on a patient with a catheter or guide wire for instance, automatic recognition of the catheter is carried out with recorded x-ray images using a computer system. The x-ray image recording parameters are changed on the basis of the determined quality of the imaging of the object, with the x-ray device preferably being automatically activated with the changed x-ray image recording parameters, to record x-ray images. The doctor can therefore concentrate on the actual intervention and does not have to worry about operating the x-ray device.

11 Claims, 2 Drawing Sheets

METHOD FOR GENERATING AN X-RAY IMAGE SEQUENCE

CROSS REFERENCE TO RELATED APPLICATIONS

This application claims priority of German application No. 10 2005 030 364.1 filed Jun. 29, 2005, which is incorporated by reference herein in its entirety.

FIELD OF THE INVENTION

The invention relates to a method for generating an x-ray image sequence as well as an x-ray image recording system with an x-ray device and a computer system.

BACKGROUND OF THE INVENTION

Minimally invasive interventions on patients are carried out particularly for the purposes of diagnosis or smaller operations in the body of a patient. Certain objects, for instance catheters or guide wires, are hereby inserted into the body of the patient. To this end, an x-ray image recording system is hereby frequently used to track the specific objects, i.e. to image the specific objects in the patient environment.

One problem in the prior art is the optimization of the x-ray image recording parameters. The number of adjustable parameters increases as the functionality of x-ray image recording systems increases. It was hitherto left to the user to adjust these parameters as well as possible. This is however not always done perfectly, since the user is concentrating on the actual intervention and diagnosis. Facilities with plenty of human resources occasionally have additional personnel who attend exclusively to the adjustment of the x-ray image parameters.

WO 03/059166 A2 discloses the use of an image data processing device in conjunction with the recording of x-ray images. The imaging of body prostheses in x-ray images in particular is mentioned as the field of application. A reference image is recorded, in which the parameters of the x-ray image recording system are set as optimally as possible. This above all concerns the position of the structure to be imaged in the x-ray image. If an image is recorded at a later time, the contours of the imaged structure are automatically evaluated and it is indicated to a user via a monitor how he/she has to change the parameters of the x-ray image recording system in order to reproduce the situation of the reference image recorded at the start. With one embodiment activation can be carried out automatically. Aside from controlling the position of the imaged structure in the x-ray image, further parameters can also be considered, for instance the voltage present at the x-ray light generator and current passed through. The parameters can also be adjusted as a function of the gray-scale values in an image. To this end, in WO 03/059166 A2, a calibration phantom is introduced into the image region in addition to the imaged object.

SUMMARY OF THE INVENTION

It is the object of the invention to optimize the generation of an x-ray image sequence for the purpose of supporting an intervention and/or a diagnosis process. The object is achieved by a method and an x-ray image recording system according to the claims.

The method according to the invention comprises the steps that the x-ray image recording parameters are first adjusted at an x-ray device. This is generally carried out manually, however the settings from the previous time can also be adopted automatically. An x-ray image with an object to be imaged is now recorded on the basis of the adjusted x-ray image recording parameters. In the case of an intervention, the object to be imaged is in particular an interventional instrument, a catheter for instance. The recorded x-ray image is now subjected to automatic computer object recognition using a computer system and a variable is determined which represents the quality of the imaging of the object. Furthermore, the computer system automatically determines an adjustment of at least one of the x-ray image recording parameters on the basis of the determined variable and the settings of the x-ray device are accordingly changed, preferably automatically activated by the computer system. Further x-ray images can then be recorded, with the steps of object recognition and adjustment of the x-ray parameters being able to be repeated as often as necessary.

The invention thus utilizes the possibilities of computer technology automatically to recognize image objects. Methods exists for this purpose in the prior art, which need not be described here in detail. The image definition, the absolute brightness and/or the contrast are considered inter alia as the variable which represents the quality of the image of the object. This is at least qualitatively possible even with poor x-ray images. In extreme cases, the variable can also be a logical variable, which indicates whether a corresponding threshold value was exceeded or not.

The coordinates for a patient table position, i.e. the coordinates of the patient table in the X and Y direction as well as the height Z are considered as x-ray image recording parameters in modern x-ray image recording systems, as are the settings of an x-ray collimator, i.e. of lead plates, which shield many regions of the image object (the patient) from the x-rays and variables relating to the x-ray quantity, such as the high voltage at the x-ray tube, the pre-filtering setting, e.g. in the case of pre-filtering with copper (thickness in mm), the image rate and/or the image frequency or the detector dose at the x-ray detector are also considered.

Modern computer systems are not only able to recognize the object itself, but they can also evaluate the area around the object analytically. The computer system used here in the field of medical engineering can thus determine whether and where structures are imaged in the area around the object in the x-ray image. In the case of a catheter, it can be of interest whether bone structures are imaged. Since these can adversely affect recognition of a catheter, the direction from which the x-ray image is recorded can optionally be changed. The [lacuna] is possible in a particularly easy manner in the case of an x-ray device with C-arm, in which the angulation of the x-ray C-arm over at least one of two angulation axes or even the distance of the detector from the x-ray source (x-ray radiation) can be adjusted as a function of the computer-detected area around the object in the x-ray image. A minimal distance from a catheter tip to the imaged bones can be determined in the computer for instance and a three-dimensional evaluation of x-ray image data can ensure corresponding control commands for the x-ray C-arm. The invention also includes collectively subjecting several x-ray images to automatic computer object recognition, such that three-dimensional evaluations of this type are possible.

The x-ray recording system according to the invention comprises an x-ray device and a computer system, with the x-ray device being designed automatically to recognize specific objects in images recorded by the x-ray device. In accordance with the invention, the computer system is designed to determine a variable relating to the quality of the imaging of the specific objects in the recorded images and to activate the x-ray device as a function of this variable.

Automatic activation of the x-ray device means that the user does not actually have to operate the x-ray device and the x-ray recording system as a whole during the intervention and need not monitor the quality of imaging him/herself. He/she can focus on his/her actual task in respect of the patient. Additional personnel are no longer required to adjust the x-ray image recording parameters.

BRIEF DESCRIPTION OF THE DRAWINGS

A preferred embodiment of the invention is now described with reference to the drawing, in which.

DETAILED DESCRIPTION OF THE INVENTION

Figure 1:
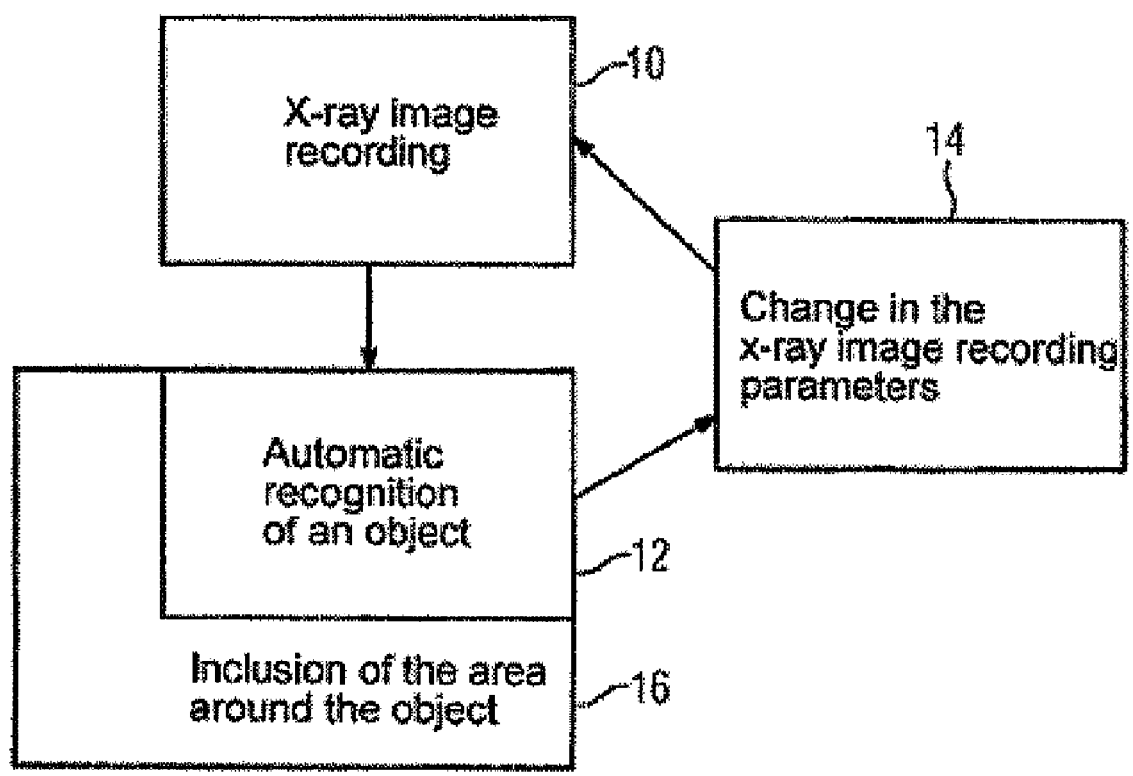
FIG. 1 shows the steps of the method according to the invention.

An intervention is carried out on a patient using a catheter, by a cardiologist in the heart of a patient for instance. The cardiologist monitors the position of the catheter on the basis of x-ray images. After a basic adjustment of the x-ray recording parameters, by the cardiologist him/herself for instance or by an operator at the x-ray image recording system, a first x-ray image recording is carried out in step 10. As a rule the catheter can be easily recognized on this x-ray image. It is thus possible to subject the x-ray image or even a plurality of x-ray images together to automatic computer object recognition (Step 12). The computer system of the x-ray recording system used, an x-ray angiography system for instance, must be designed correspondingly for the automatic recognition of objects in the recorded images.

As the x-ray image data is generated in computer-readable form anyway and displayed on a computer monitor, only corresponding software must be used. The computer system now determines at least one variable relating to the quality of the imaging of the catheter. Conventional means enable corresponding variables for image definition, absolute brightness and also contrast to be defined and determined. The variable provides information about the degree to which the catheter can be recognized. Further such variables can also be defined and used.

On the basis of the variables, it is possible to determine whether or not the previous x-ray image recording parameters are suitable. The x-ray image recording parameters can also include the coordinates for the patient table position for instance.

If the catheter is located right at the edge of the image, the patient table can advantageously be moved so that the catheter is located in the center of the image.

An x-ray collimator of the x-ray image recording system can likewise be adjusted such that only the area of interest with the imaged object (catheter) is radiated, thereby helping to reduce patient exposure to radiation.

If the contrast or the image definition of the recognizable object is particularly good, it can be concluded that it would also be possible to achieve qualitatively adequate x-ray images even with less exposure to radiation. Parameters relating to the x-ray quantity can be changed correspondingly. These include the high voltage at the x-ray tube, the detector dose of the x-ray detector or even the image frequency in systems, in which several images are recorded repeatedly one after the other, for instance if the catheter is moved and this is to be monitored on the basis of the images.

After an object has been automatically recognized in step 12, a change in the x-ray image recording parameters can be determined in step 14 by the computer system and a corresponding adjustment can be carried out at the x-ray image recording system in an automatically controlled manner. The previous x-ray image recording is then continued, with only one x-ray image being able to be recorded again or a whole sequence of x-ray images. The automatic recognition of the object in step 12 is advantageously repeated and the x-ray image recording parameters are regularly adjusted to the recorded images in step 14.

The area around the object is also included in advanced technology (step 16). In the case of the example given of an examination of the heart with a catheter by cardiologists, the bones of the spinal column and the ribs in particular can cause interference.

Advanced object recognition technology allows structures different from the object, i.e. the catheter, also to be detected (for instance on the basis of a threshold value criterion relating to the brightness in the image). In other words, the computer system can recognize which structures in the x-ray image are bones. These structures interfere with the imaging of the catheter. It can thus be desirable to rotate the imaging direction such that the bones are at a certain distance from the catheter. Such a rotation is particularly easy with an x-ray device with an x-ray C-arm (for instance an x-ray angiography system), where the angular position (angulation) of the x-ray C-arm can be defined about two axes. Furthermore, the distance of the x-ray detector from the x-ray emitter can be adjusted at the C-arm. Thus a change in the x-ray image recording parameters can again be expedient here, with the angulations of the C-arm and the distance of the detector from the x-ray emitter being included in the x-ray recording parameters. Repeated x-ray image recording can take place accordingly. If the cardiologist moves the catheter in the direction of the heart, repeated adjustment of the parameters may be required. It is optionally expedient that the change in the x-ray image recording parameters can be requested and/or triggered by the cardiologist him/herself, by activating corresponding input keys at the computer system for instance.

Figure 2:
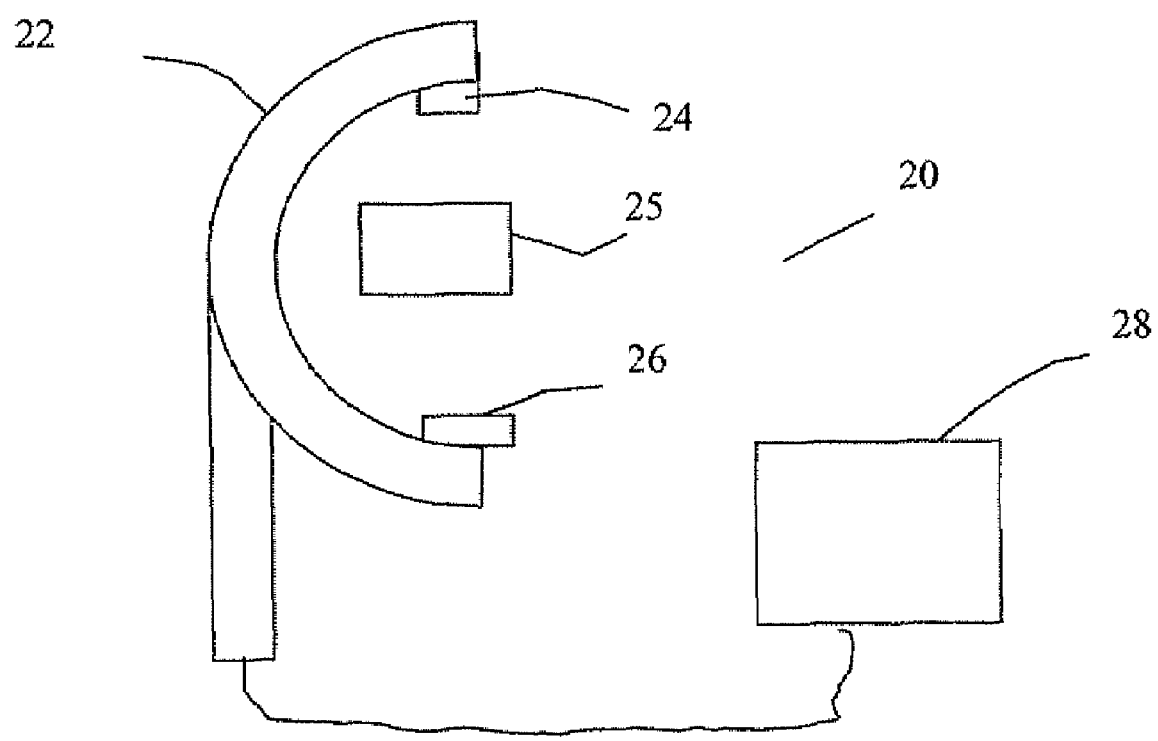
FIG. 2 shows an x-ray system according to an embodiment of the invention.

FIG. 2 shows an x-ray imaging system 20, in which the described method can be implemented. The x-ray system 20 includes a C-arm 22, which can be moved freely about a patient support 25 and has an x-ray emitter 24 and an x-ray detector 26 attached to it arms. The system 20 comprises a computer 28 that controls the position of the C-arm 22.

The invention allows the cardiologist to concentrate on the job in hand, i.e. inserting the catheter, whilst the x-ray image recording parameters are adjusted to an optimum during the recording of an x-ray image sequence. The catheter is imaged in the center of the image in an optimum manner and the exposure to radiation is such that the catheter can easily be recognized on the images without the exposure to radiation being excessively high.

The invention claimed is:

1. A method for generating a medical x-ray image sequence with a medical x-ray device, comprising:
adjusting a first x-ray image recording parameter of the x-ray device;
recording an x-ray image of an object to be imaged using the adjusted x-ray device, the object to be imaged is an interventional instrument;
subjecting the recorded x-ray image to a computer system for an automatic computer object recognition and a determination of a variable relating to a quality of an imaging of the object to be imaged, wherein the computer system determines whether a structure in an area around the object in the x-ray image is imaged;

determining an adjustment of the first or a second x-ray image recording parameter by the computer system based on the variable;

changing a setting of the x-ray device based on the adjustment, wherein an x-ray device with an x-ray C-arm is used and an angulation of the x-ray C-arm over an axis and a distance of an x-ray detector from an x-ray emitter are adjusted as a function of a computer-detected area around the object; and further recording a further x-ray image using the changed setting x-ray device.

2. The method as claimed in claim 1, wherein the computer system detects an image definition, an absolute brightness, or a contrast of the object in the x-ray image.

3. The method as claimed in claim 1, wherein the first and second x-ray image recording parameters are selected from the group consisting of: a coordinate of a patient table position, a setting of an x-ray collimator, and a parameter relating to an x-ray quantity.

4. The method as claimed in claim 3, wherein the parameter relating to the x-ray quantity is selected from the group consisting of: a high voltage of an x-ray tube, a pre-filtering thickness, an image frequency, and a detector dose of an x-ray detector.

5. The method as claimed in claim 1, wherein the subjecting, determining, changing, and further recording steps are repeated.

6. The method as claimed in claim 1, wherein the object to be imaged is a catheter in an intervention procedure.

7. The method as claimed in claim 1, wherein the adjusted x-ray image recording parameter based on the variable is the first x-ray image recording parameter of the x-ray device.

8. The method as claimed in claim 1, wherein the adjusted x-ray image recording parameter based on the variable is not the first x-ray image recording parameter of the x-ray device.

9. The method as claimed in claim 1, wherein the computer system automatically changes the setting of the x-ray device based on the adjustment.

10. A method for generating a medical x-ray image sequence with a medical x-ray device, comprising:

adjusting a first x-ray image recording parameter of the x-ray device;

recording an x-ray image of an object to be imaged using the adjusted x-ray device;

subjecting the recorded x-ray image to a computer system for an automatic computer object recognition and a determination of a variable relating to a quality of an imaging of the object to be imaged, and wherein the computer system determines whether a structure in an area around the object in the x-ray image is imaged;

automatically determining an adjustment of the first or a second x-ray image recording parameter based on the variable and automatically changing a setting of the x-ray device based on the adjustment, and wherein the method uses an x-ray device with an x-ray C-arm and an angulation of the x-ray C-arm over an axis and a distance of an x-ray detector from an x-ray emitter are adjusted as a function of a computer-detected area around the object; and further recording a further x-ray image using the changed setting x-ray device.

11. A medical x-ray image recording system, comprising:

an x-ray device; and a computer system that:

automatically recognizes an object in an image recorded by the x-ray device, and whether a structure in an area around the object is imaged, wherein the object to be imaged is a catheter in an intervention procedure, determines a variable relating to a quality of an imaging of the object in the image, and automatically activates the x-ray device as a function of the variable.

* * * * *